(12) United States Patent
Larsson et al.

(10) Patent No.: US 6,967,101 B1
(45) Date of Patent: Nov. 22, 2005

(54) SURFACE AND ITS MANUFACTURE AND USES

(75) Inventors: Anders Larsson, Bromma (SE); Anette Ocklind, Upplands-Vasby (SE); Helene Derand, Taby (SE)

(73) Assignee: Gyros AB, Uppsala (SE)

( * ) Notice: Subject to any disclaimer, the term of this patent is extended or adjusted under 35 U.S.C. 154(b) by 0 days.

(21) Appl. No.: 09/937,533

(22) PCT Filed: Mar. 24, 2000

(86) PCT No.: PCT/EP00/02632

§ 371 (c)(1),
(2), (4) Date: Nov. 27, 2001

(87) PCT Pub. No.: WO00/56808

PCT Pub. Date: Sep. 28, 2000

(30) Foreign Application Priority Data

Mar. 24, 1999 (SE) .................................. 9901100

(51) Int. Cl.[7] ........................... C12N 5/00; C12M 1/00; H05H 4/00; G01N 21/00
(52) U.S. Cl. .................. 435/402; 435/307.1; 427/446; 422/57
(58) Field of Search ................ 435/398, 402, 435/3, 7.1; 427/446; 422/82.08, 57

(56) References Cited

U.S. PATENT DOCUMENTS

| | | | |
|---|---|---|---|
| 4,022,954 A | 5/1977 | Kurosawa et al. | |
| 4,741,619 A | 5/1988 | Humphries et al. | |
| 5,124,173 A | 6/1992 | Uchiyama et al. | |
| 5,376,252 A | 12/1994 | Ekstrom | |
| 5,399,316 A | 3/1995 | Yamada | |
| 5,690,841 A | 11/1997 | Elderstig | |
| 5,773,488 A | 6/1998 | Allmer | |
| 5,962,081 A | 10/1999 | Ohman | |
| 5,995,209 A | 11/1999 | Ohman | |
| 6,022,553 A * | 2/2000 | Anders et al. | 424/411 |
| 6,027,695 A | 2/2000 | Oldenburg et al. | |
| 6,126,765 A | 10/2000 | Ohman | |
| 6,143,247 A * | 11/2000 | Sheppard et al. | 422/63 |
| 6,144,447 A | 11/2000 | Ohman | |
| 6,192,768 B1 | 2/2001 | Wallman | |
| 6,203,291 B1 | 3/2001 | Stemme | |
| 6,322,682 B1 | 11/2001 | Arvidsson | |
| 6,454,970 B1 | 9/2002 | Ohman | |
| 6,620,478 B1 | 9/2003 | Ohman | |
| 6,632,656 B1 | 10/2003 | Thomas | |
| 6,653,625 B2 | 11/2003 | Andersson | |
| 6,685,743 B2 * | 2/2004 | Komvopoulos et al. | 623/18.11 |
| 6,717,136 B2 | 4/2004 | Andersson | |
| 6,728,644 B2 | 4/2004 | Bielik et al. | |
| 6,811,736 B1 | 11/2004 | Ohman | |
| 6,812,456 B2 | 11/2004 | Andersson | |
| 6,812,457 B2 | 11/2004 | Andersson | |
| 2003/0044322 A1 | 3/2003 | Andersson | |
| 2003/0047823 A1 | 3/2003 | Ohman | |
| 2003/0053934 A1 | 3/2003 | Andersson | |
| 2003/0054563 A1 | 3/2003 | Ljungstrom | |
| 2003/0082075 A1 | 5/2003 | Agren | |
| 2003/0094502 A1 | 5/2003 | Andersson et al. | |
| 2003/0129360 A1 | 7/2003 | Derand | |
| 2003/0156763 A1 | 8/2003 | Soderman | |
| 2003/0211012 A1 | 11/2003 | Bergstrom | |
| 2003/0213551 A1 | 11/2003 | Derand | |
| 2003/0231312 A1 | 12/2003 | Sjoberg | |
| 2004/0058408 A1 | 3/2004 | Thomas | |
| 2004/0096867 A1 | 5/2004 | Andersson | |
| 2004/0099310 A1 | 5/2004 | Andersson | |
| 2004/0120856 A1 | 6/2004 | Andersson | |
| 2004/0202579 A1 | 10/2004 | Larsson et al. | |

FOREIGN PATENT DOCUMENTS

| | | |
|---|---|---|
| AT | 404099 | 1/1998 |
| EP | 0 106 046 A2 | 4/1984 |
| EP | 0 106 662 A2 | 4/1984 |
| EP | 0 111 795 A2 | 6/1984 |
| EP | 0 467 639 A2 | 1/1992 |
| GB | 2 061 969 A | 5/1981 |
| GB | 2238791 | 6/1991 |
| GB | 2244276 | 11/1991 |
| WO | WO 96/18498 | 6/1996 |
| WO | WO 97/21090 | 6/1997 |
| WO | WO-982743 | 6/1998 |
| WO | WO-9855231 | 12/1998 |
| WO | WO-9919717 | 4/1999 |
| WO | WO 99/58245 | 11/1999 |

OTHER PUBLICATIONS

Chang et al. "Amination of Polycarbonate Surface and Its Application for Cell Attachment" Art. Cells, Blood Subs., and Immob. Tech. 27(3): 229-244 (1999).*

(Continued)

*Primary Examiner*—Jean C. Witz
*Assistant Examiner*—Susan Hanley
(74) *Attorney, Agent, or Firm*—Fulbright & Jaworski L.L.P.

(57) ABSTRACT

A method for rendering a surface covered by a plastic material more hydrophilic by treatment with a gas plasma non-polymerizable gas. The method is characterized in that the intensity of the plasma is selected so that the surface becomes permanently more hydrophilic. Also disclosed is a naked plasma treated surface of plastic having an immediate water contact angle of $\leq 30°$, said water contact angle is changed ±20 and/or less than 5% upon washing with an ethanol/water mixture (70% w/w).

22 Claims, No Drawings

OTHER PUBLICATIONS

Dekker et al. "Adhesion of Endothelial cells and adsorption of SerumProteins on Gas Plasma-Treated Polytetraflouroethylene" Biomaterials 12(2): 130-8 (1991).*
Webter's II New Riverside University Dictionary (Houghtin Mifflin: Boston MA) 1984, p. 667.*
U.S. Appl. 10/169,056, Andersson et al.
U.S. Appl. 10/276,282, Larsson et al.
U.S. Appl. 10/402,138, Kylberg et al.
U.S. Appl. 09/958,577, Ulfendahl.
U.S. Appl. 09/869,554, Orlefors et al.
U.S. Appl. 09/830,475, Stjemstrom.
U.S. Appl. 10/168,942, Tooke et al.
U.S. Appl. 10/957,452, Ekstrand et al.
U.S. Appl. 10/070,912, Ohman et al.
U.S. Appl. 10/402,137, Kylberg et al.
U.S. Appl. 10/030,297, Derand et al.
U.S. Appl. 10/924,151, Tooke et al.
U.S. Appl. 10/513,084, Holmquest et al.
U.S. Appl. 09/937,533, Derand et al.
U.S. Appl. 10/999,532, Ostlin et al.
U.S. Appl. 10/867,893, Derand et al.
U.S. Appl. 11/017,252, Derand et al.
U.S. Appl. 10/182,792, Derand et al.
U.S. Appl. 10/450,177, Ohman et al.
U.S. Appl. 10/129,032, Tormod.
U.S. Appl. 09/674,457, Larsson et al.
U.S. Appl. 10/069,827, Derand et al.
U.S. Appl. 10/244,667, Agren.
U.S. Appl. 10/849,321, Fielden et al.
U.S. Appl. 10/111,822, Tooke et al.
Bergstroem et al. "Effects of Polymerization Conditions when Making Norbornene—Ethylene Copolymers using the Metallocene Catalyst Ethylene Bis (Indenyl) Zircornium Dichloride and Mao to Obtain High Glass Transition Temparture," Journal of Applied Polymer Science, vol. 63 No. 8, Feb. 22, 1997, pp. 1063-1070.

* cited by examiner

SURFACE AND ITS MANUFACTURE AND USES

The present invention concerns a method for enhancing the hydrophilicity of a polymer surface by treatment with a plasma.

A common method for surface modification of plastics is to subject them to various forms of plasma treatment (Chan et al., Surface Science Reports 24 (1996) 1–54; and Garbassi et al, Polymer Surfaces—From Physics to Technology, John Wiley (1998) 238–241). This is done in a plasma reactor, which is a vacuum vessel with a gas at low pressure (typically 10 to 1000 mTorr). When a high frequency electric field is applied over the reactor, a plasma (also called glow discharge) is formed, containing reactive species like ions, free radicals and vacuum-UV photons. These species react with the plastics surface and cause a chemical modification with properties depending on the nature of the gas and on the plasma parameters. Gases like oxygen and argon are typically used for hydrophilisations and adhesion improvement on nonpolar plastics, while vapours of polymerising monomers can be used to apply thin coatings on plastics for a number of different purposes (Yasuda, Plasma Polymerization, Academic Press 1985.

There are a number of publications on treatment of polycarbonate surfaces with oxygen and argon plasmas. A stability study (Morra et al, Angew. Makromol. Chem. 189(3184) (1991) 125–136) showed that much of the hydrophilicity of the treated surfaces was lost after either water extraction or 3 days' dry storage. The hydrophilicity loss after water extraction was due to the formation of low molecular weight water-soluble surface species during the plasma treatment. The storage instability was attributed to rearrangement of the polymer chains in the surface. An ESCA study (Greenwood et al., Macromolecules 30 (1997) 1091–1098) showed that 79% of the oxygen incorporated in the polycarbonate surface by oxygen plasma treatment was removed by washing with a 1:1 cyclohexane/isopropanol mixture. This is attributed to degradation of polymer chains during the plasma treatment.

Similar effects have also been observed for polystyrene. An ESCA-study of a plasma-treated tissue-culture polystyrene showed about 35% loss of surface oxygen after water washing (Onyiriuka et al., J. Coll. Interf. Sci. 144(1) (1991) 98). In two other ESCA studies, oxygen-plasma treated polystyrene gave 25% surface oxygen loss after water washing (Callen et al., J. Vac. Sci. Technol. A 13(4) (1991) 2023–2029), (Morra et al., Angew. Macromol. Chem. 189 (3184) (1991) 125–136). A polystyrene surface treated with an oxygen plasma had initially a water-contact angle of 7°, but after a methanol wash the contact angle increased to 64° (Murakami et al., J. Coll. Interf. Sci. 202 (1998) 37–44).

WO 9618498 describes an attempt to produce a permanently hydrophilised surface made of plastics. The method comprises a first step in an inorganic gas plasma in order to introduce charges on the surface and a second step during which a polyionic polymer having the opposite charge is adsorbed to the surface.

EP-A-106,046 describes hydrophilisation of fluorinated polymer surfaces by treatment in a gas plasma in which the main component is a polymerising nitrogen-containing organic compound.

GB 2,061,969 describes the manufacture of hydrophilic and antistatic vinyl chloride polymer by treatment in an inorganic gas plasma. The problem of rendering the plastics permanently hydrophilic is not mentioned.

DE 3712491 describes gas plasma hydrophilization of porous membranes made of various synthetic polymers. Plastic material is not mentioned. Storage stability of the hydrophilized membranes is indicated but there is no discussion related to stability during washing conditions in aqueous milieu. Liquid contact angles are measured, but since porous surfaces typically gives significantly decreased angles compared to no-porous smooth surfaces, these values cannot simply be compared with the values given in this specification.

EP 106662 describes a microtiter plate made of a dark plastic material in order to improve fluorescence measurements in the wells. Microtiter plates are normally devoid of liquid transportation systems in microformat.

The electric excitation field applied typically has a frequency in the radiowave or microwave region, i.e. kHz-MHz or GHz respectively. The modification (hydrophilisation) on the polymer surface caused by the plasma will depend mainly on a number of internal plasma parameters such as: type of species present in the plasma, spatial distributions, energy distributions and directional distributions. In turn these parameters depend in a complex way on the external plasma parameters: reactor geometry, type of excitation, applied power, type of process gas, gas pressure and gas flow rate.

In many applications involving contact between polar liquids and surfaces it is of no big concern whether an introduced hydrophilicity is stable towards washing or not. Particular problems are encountered in case the polymer surface is part of a channel of capillary dimensions, where a high degree of hydrophilicity is necessary if aqueous liquids are to be introduced by self-suction or by centripetal forces. This becomes particularly true in case a repeated contact is to take place reproducibly, in which case an unstable surface modification will be washed away during the first liquid contact. The smaller dimensions of the channel the more severe the problem becomes.

In the context of the invention the expression "plasma treated surface" will, if not otherwise specified, refer to an uncoated naked plasma treated surface, possibly being derivatized to contain separate reactive species firmly bound to the surface.

Cell culturing in microfabricated devices has been described previously in for instance WO 9955827 with priority from Apr. 27, 1998.

WO 9721090 relates to a microfluidic device in which centrifugal force is used to drive the liquids. In one sentence it is suggested that microculture and identification of pathogens can be made within the device without any hint at the selection of the proper surface characteristics.

Cell aggregates have previously been cultured in vessels with a water contact angle below 30° (JP patent application 19930119579, Derwent abstract accession number 1995-047885.

Adherence of cells to gas plasma treated polytetrafluoro ethylene (PTFE) surfaces with water contact angles 20–45° has been studied (Dekker et al., Clinical Materials 11 (1992) 157–162). Adherence appears to have required abnormally high concentrations of substances promoting adherence (20% human serum-containing culture medium) compared to the most commonly used 10% or less.

Adherence of CHO cells to surfaces which have been gas plasma hydrophilised in the presence of $H_2O$-vapour has been studied in order to look for optimal cell cultivation properties of plastic surfaces (Lee et al., Biomaterials 12(5) (1991) 443–448). Poor cell adherence to the most hydrophilic surfaces was found found.

Microfluidic devices in which liquid transportation systems are defined by hydrophilic/hydrophobic barriers have been described previously in for instance WO 9958245 with priority from May 8, 1998.

Experimental results partly corresponding to this invention have been presented at the Second International Symposium on Polymer Surface Modification, New Ark June 1999 (Anders Larsson: Plasma Treated Polycarbonate as Substrate for Culture of Adherent Mammalian Cells).

OBJECTIVES OF THE INVENTION

A first objective is to provide a gas plasma method for hydrophilisation of polymer surfaces, which enhances the stability of the hydrophilicity introduced.

A second objective is to provide plasma treated surfaces that are hydrophilic after the treatment and remain so upon repeated wetting/drying, i.e. have an initial hydrophilicity that is not significantly altered in contact with hydrophilic liquids, for instance etanol/water mixtures.

A third objective is to provide capillary/channel/chamber system, for instance in microfabricated form, having capillaries/channels/chamber, the inner surfaces of which being as defined for the second objective and permitting repeated introduction of aqueous solutions in a reproducible way.

A fourth objective is to provide liquid transportation systems in which at least a part of the inner surfaces complies with the second objective.

A fifth objective is to provide plasma treated surfaces that can be used for cell culturing, assay reactions etc.

These objectives are mainly adapted to surfaces that before the plasma treatment have a relatively high immediate water-contact angle, for instance $\geq 20°$, such as $\geq 30°$ or even $\geq 50°$. By the term "immediate water-contact angle" is meant that the contact angle is measured on a dry surface before an applied liquid has significantly evaporated. See the experimental part.

The Invention

We have now discovered that the objectives given above can be meet, if the polymer surface (plastics surface) is brought into contact with a gas plasma of high intensity (energy input per gas molecule). Our discovery is explainable in terms of two types of polar groups being introduced: (1) Groups retained firmly on the polymer surface and (2) groups allocated to loosely held degradation fragments. The first alternative will result in a stable hydrophilicity. The second alternative will result in a hydrophilicity, which is easily removed by contact with polar liquids, such as aqueous solutions.

Accordingly a first aspect of the invention is a method for rendering a polymer surface (plastics surface) permanently more hydrophilic by contacting the surface with a gas plasma so that firmly bound polar groups are introduced on the surface. Most likely these polar groups are introduced directly on the polymer skeleton constituting the surface, possibly involving cross-linking of the surface layer.

Hydroxy and or amino groups, carboxy groups, ether groups etc and other groups in which a carbon atom binds to a heteroatom selected among oxygen, sulphur, and nitrogen are examples of polar groups that may be introduced. Changes in surface presence of this type of groups may be studied by ESCA (XPS).

The expressions "permanently more hydrophilic" and "stable hydrophilicity" contemplate that the immediate water-contact angle remains essentially unchanged upon washing with ethanol (70% w/w, washing procedure as given in the experimental part). This means that that the washing procedure should not be allowed to change the immediate water-contact angle more than ±20% and/or more than ±5°.

The storage stability (in dry form) of the hydrophilised surface should be at least one month with acceptable increases in immediate water-contact water angle not being larger than 10°, preferably not larger than 5°. In case the storage stability in dry form is not acceptable, sufficient storage stability often can be accomplished by storing in aqueous atmosphere or in an aqueous liquid.

The method of the invention may have an optional washing step subsequent to the gas plasma treatment step. This washing procedure means contacting the gas plasma treated surface with an aqueous solution or some other polar liquid to remove loosely held hydrophilic compounds. The washing solution is preferably water, a water-miscible liquid or a mixture of these. Examples of water-miscible liquids are methanol, ethanol, isopropanol, n-propanol, t-butanol, sec-butanol, dimethyl formamide, dimethyl sulphoxide, acetone and other liquid compounds having similar solubilities in water.

The required intensity of the plasma will depend on the variables discussed above. Satisfactory gas plasmas may be found in case the electric excitation power applied is $\geq 250$ W with preference for $\geq 300$ W, and typically $500 \pm 100$ W with a gas flow selected in the interval of $\leq 50$ cm$^3$/min, with preference for $\leq 25$ cm$^3$/min. For the plasma intensity, the interval is normally $\geq 5$ W/cm$^3$/min, such as $\geq 10$ W/cm$^3$/min or $\geq 20$ W/cm$^3$/min or even $\geq 35$ W/cm$^3$/min. Normalised values per m$^2$ electrode area will typically be $\geq 30$ W/m$^2$/cm$^3$/min, such as $\geq 60$ W/m$^2$/cm$^3$/min or $\geq 120$ W/m$^2$/cm$^3$/min or even $\geq 215$ W/m$^2$/cm$^3$/min. The pressures are typically lower than 100 mTorr, with preference for pressures that are $\leq 50$ mTorr. These ranges apply for a temperature of 25° C., atmospheric pressure and oxygen. For other gases the values must be multiplied with $M_{O2}/M_x$, where $M_{O2}$ and $M_x$ are the molecular weights of oxygen and the other gas, respectively.

The gases used should be non-polymerisable in the type of plasma contemplated. Typical such gases are inorganic. This means that suitable gases are found among oxygen, nitrogen, noble gases (such as helium, neon, argon, krypton, xenon) and mixtures thereof, such as air and mixtures containing other proportions of oxygen and nitrogen. Other potentially useful gases are carbon dioxide, carbon monoxide, water vapour etc that might be used either solely or in combination. By varying the composition of gas the groups inserted onto the surface it is likely that the groups can be varied with respect to kinds and density.

Illustrative examples of polymerisable gases are volatile lower organic molecules such as lower hydrocarbons and vapours of allyl- or acryl monomers, aromatics etc. An inorganic non-polymerisable gas may be present together with a polymerisable organic compound in gas form.

Plasma reactor vessels enabling a sufficiently high power output combined with proper gas flow velocities are commercially available. As stated above the reactor vessels should enable an electric excitation power input for instance in the microwave or radio wave ranges. A suitable plasma reactor is PS0500 (BOC Coating Technology, USA) which permits a radiofrequency (RF) power of 0–500 W and gas flow of 0–100 or 0–1000 standard cm$^3$/min.

The results of a treatment may depend on the design of the reactor vessel used meaning that the optimal interval to a certain degree will vary from one reactor design to another.

The results may also depend on where in the reactor the surface is placed during the treatment.

The immediate water-contact angle of the polymer material (plastics) covering the surface to be gas plasma treated is typically $\geqq 20°$. The largest advantages with the invention are obtained for polymer materials that provide larger immediate water-contact angles, such as $\geqq 30°$ for instance $\geqq 50°$. These figures refer to plastic surfaces having been cleaned with respect to water-soluble compounds and low molecular weight compounds (typically $\leqq 1$ kD). Illustrative examples of how the water-contact angle may vary with polymer are given in table 1.

The inventive method typically results in an increase in the permanent hydrophilicity which corresponds to lowering the immediate water contact angle of the initial plastics surface more than 20%, such as more than 50% (after removal of water-soluble compounds, low molecular weight compounds and the like). A large increase in hydrophilicity is more important for hydrophobic than for hydrophilic plastics.

TABLE 1

| Plastic | Water-contact angle |
| --- | --- |
| PTFE (Teflon) | 108° |
| Silicone rubber (Sylgard 184) | 106° |
| Polypropylene | 95° |
| Polyethylene | 94° |
| Polystyrene | 90° |
| Polycarbonate | 78° |
| PET (polyester) | 76° |
| Styrene-acrylonitrile | 73° |
| PMMA (Plexiglas) | 59° |

Typically the polymer on the surface has been obtained by polymerisation of monomers comprising unsaturation, such as in carbon-carbon double bonds or carbon-carbon-triple bonds. The polymer may be a homopolymer or a copolymer.

The monomers may, for instance, be selected from mono-, di and poly/oligo-unsaturated compounds, e.g. vinyl compounds and other compounds containing unsaturation. The monomers may or may not contain halogen substituents, such as fluoro and/or chloro. Illustrative monomers are:

(i) alkenes/alkadienes (such as ethylene, butadiene, propylene and including substituted forms such as vinyl ethers), cycloalkenes, monofluorovinyl and di- and polyfluorovinyl hydrocarbons (for instance tetrafluoroethylene), alkene-containing acids, esters, amides, nitrites etc for instance various methacryl/acryl compounds; and (ii) vinyl aryl compounds (such as mono-, di- and trivinyl benzenes) that optionally may be substituted with for instance lower alkyl groups (C1–6) etc.

Another type of polymers are condensation polymers in which the monomers are selected from compounds exhibiting two or more groups selected among amino, hydroxy, carboxy etc groups (so called polyfunctional compounds). Particularly emphasised monomers are polyamino monomers, polycarboxy monomers (including corresponding reactive halides, esters and anhydrides), poly hydroxy monomers, amino-carboxy monomers, amino-hydroxy monomers and hydroxy-carboxy monomers, in which poly stands for two, three or more functional groups. Polyfunctional compounds include compounds having a functional group that is reactive twice, for instance carbonic acid or formaldehyde. The polymers contemplated are typically polycarbonates, polyamides, polyamines, polyethers etc. Polyethers include the corresponding silicon analogues, such as silicone rubber.

The polymers may be in cross-linked form.

The polymer on the surface may be a mixture of two or more different polymer(s)/copolymer(s). In this case the water-contact angles and their changes discussed above apply to these mixtures, i.e. the factual surface.

Particularly interesting polymers are those that have a non-significant fluorescence for excitation wavelengths in the interval 200–800 nm and emission wavelengths in the interval 400–900 nm. By non-significant fluorescence is meant that the fluorescence intensity in the above-given emission wavelength interval should be below 50% of the fluorescence intensity for a reference plastics (=a polycarbonate of bisphenol A without fluorescent additives). In fact it does not harm in case the fluorescence intensity of the plastics is even lower, such as <30% or <15%, such as <5% or <1%, of the fluorescence intensity of the reference plastics. Typical plastics having an acceptable fluorescence are polymers of aliphatic monomers containing polymerisable carbon-carbon double bonds, such as polymers of cykloalkenes (e.g. norbornene and substituterade norbornenes), ethylene, propylenes etc, as well as other non-aromatic polymers of high purity, e.g. certain grades of polymethylmethacrylate.

The requirement for a low fluorescence is of particular importance in case the plastics are to be used for carrying samples in which one or more fluorescent substances are to be detected/measured. It then becomes important to select plastics with non-significant fluorescence at the wavelength at which a fluorescent substance to be detected/measured fluoresces. In most cases this means that the fluorescence intensity of the plastics at the emission wavelength of the substance should be below 50% of the fluorescence intensity of the substance. In fact it will not harm in case the fluorescence intensity of the plastics is <30%, such as <15%, or still lower, such as <5% or <1%, of the fluorescence intensity of the substance. In case the fluorescence of several substances emitting light at different wave-lengths are to be measured it will put harsher demands on the plastics, since fluorescence of the plastics then should be non-significant for broader wave-length bands or for several bands.

After the plasma treatment, optionally after a washing procedure to remove loosely held hydrophilic compounds, the surface may be further derivatized to exhibit one or more type of reactive groups, i.e. groups that are able to bind other compounds either via some type of affinity or via covalent linking. Derivatization preferably takes place after the washing step and may be preceded by a coating step, for instance, to provide the surface with a coating carrying additional hydrophilic groups that can be used for derivatization.

By masking certain parts of the surface and leaving other parts unmasked before hydrophilisation, hydrophilic patterns on a hydrophobic surface can be obtained. Alternatively a hydrophobic pattern may be printed on the surface after the hydrophilisation. These techniques may be of value in the manufacture of microfabricated liquid transportation systems. See below.

Various methods for introducing reactive groups on polymers exhibiting hydrophilic groups, such as hydroxy, amino or carboxy etc groups are well known to the averaged skilled artisan in the field. Well known affinity groups are charged groups, and groups exerting affinity via interactions of other types, possibly in combination with charge—charge interactions. Illustrative examples of charged groups are ion-exchanging groups, such as anion and cation exchanging groups, with typical examples being ammonium ions (primary, secondary, tertiary and quaternary ammonium ions), sulphates, sulphonates, phosphates, phosphonates etc. Illustrative examples of other affinity groups are so called bioaffinity groups including individual members of ligand-receptor pairs, such as antibody-antigen/hapten, complementary nucleic acids, Ig binding proteins-Ig (e.g. protein A or G-IgG), lectins-carbohydrate structures, cells-cell attachment molecules (fibronectin, collagen, RGD-peptides) etc. Included in bioaffinity groups are also semi- and fully synthetic ligands that more or less completely mimics native bioaffinity.

The hydrophilised surface may be part of arrangements of different physical forms. The hydrophilised surface may be the bottoms/walls of microtiter wells and other types of vessels and also the outer surfaces of porous and non-porous particle material. The hydrophilised surface may be part of a less hydrophilic larger surface (e.g. a hydrophobic surface).

The hydrophilised surface may provide a significant part of the liquid contact surfaces in systems intended for transport of aqueous liquids. These systems may have channels that may be of capillary dimensions, for instance with a distance between two opposite walls being $\leq 1000$ $\mu$m, such as $\leq 100$ $\mu$m, or even $\leq 10$ $\mu$m, such as $\leq 1$ $\mu$m. These systems may also contain one or more chambers connected to the channels and having volumes being $\leq 500$ $\mu$l, such as $\leq 100$ $\mu$l and even $\leq 10$ $\mu$l such as $\leq 1$ $\mu$l. The depths of the chambers may typically be in the interval $\leq 1000$ $\mu$m such as $\leq 100$ $\mu$m such as $\leq 10$ $\mu$m or even $\leq 1$ $\mu$m. The lower limit is always significantly greater than the largest of the reagents used. The lower limit is typically in the range 0.1–0.01 $\mu$m for devices that are to be delivered in dry form. One or more liquid transportation systems of this type may be placed on a common plate, for instance spinnable, such as a disc of CD-type. In the case of spinnable forms, the liquid may be forced through one or more segments of the transportation system by spinning the disc (centripetal force). In this latter case the liquid transportation systems are placed radially. Other types of pressure generating systems may also be used for transport of liquid in the liquid transportation systems discussed above.

A device having one or more liquid transportation system comprising channels and chambers with a depth $\leq 1000$ $\mu$m, such as $\leq 100$ $\mu$m or even grounder than 10 $\mu$m, such as $\leq 1$ $\mu$m, are further on called a microfabricated device. The chambers/channels are said to be in the microformat. A microfabricated device typically has its channels and chambers in one plane, such as in the surface of a plate, for instance on a disc. The plate may be circular, oval, rectangular or of any other 2D geometric form.

The channels and/or chambers are defined by liquid barriers, which are to guide a liquid flow. The liquid barriers can be in form of physical walls, bottoms and tops. Walls in form of hydrophobic barriers for guiding aqueous liquids and in form of hydrophilic barriers for guiding non-polar liquids have been suggested (WO 9955827 with priority from Apr. 27, 1998). By covering a surface (I) to be hydrophilised with a mask leaving a pattern of communicating lines and dots unmasked and hydrophilise, for instance according to the present invention, the surface (I) will exhibit a hydrophilic pattern. When placing a hydrophobic surface (II) (cover or top) against the hydrophilic pattern and leave a capillary slot between the surfaces, a liquid transportation system will be obtained. Surface (II) may also have a hydrophilic pattern matching the hydrophilic pattern of surface (I). As discussed above the hydrophilic pattern may also be obtained by hydrophilising the full surface and then print the desired hydrophobic pattern thereon. The top/cover will prevent evaporation of liquid. It may have minor parts/dots in form of through-passing holes intended for addition/removal of liquids.

An advantageous way of attaching the top/cover to the hydrophobic surface is by thermogluing as described in SE application 0000300-4, filed on Jan. 30, 2000 (which is hereby incorporated by reference). The top/cover should also allow for gas exchange between the cultivation chamber and ambient atmosphere.

Liquid transportation systems of he type referred to above may also contain valves, pumps, filters and the like.

The surface may be used for performing chemical reactions of inorganic and/or organic/biochemical nature. The surface may be used as carrier matrix in chromatography, for cell culture, for solid phase chemical synthesis of oligo/polypeptides, oligo/polynucleotides, other organic polymers and other organic compounds. Illustrative examples of reactions to be run on the surface of the invention are conventional chemical reactions or reactions that are based on affinity involving recognition through geometric fitness and interactions based on hydrogen-bonding, van-der Waals bonding, dipole—dipole interaction, charge-dipole interaction, charge—charge interaction etc. Vessels having interior surfaces being treated according to the invention may be used for storage of various types of organic and inorganic chemicals and/or liquids. For cell culturing, further details are given below.

Advantageous further developments of surfaces obtained by the present invention are described in International Patent Application PCT/EP99/10347 (which is hereby incorporated by reference). In these developments the inventive plasma hydrophilization has been applied to part of or to the complete liquid transportation system. After hydrophilization, polyethylene imine to which monomethoxy polyethylene glycol chains are bound is adsorbed to the treated surface. Preferred designs of liquid transportation systems are also described.

A second aspect of the invention is a naked plasma treated polymer surface (plastics surface) permanently hydrophilised as defined above and complying with anyone of the other above-mentioned features, either alone or in combination.

A third aspect of the invention is the various uses discussed above or below of surfaces obtained in accordance with the invention and/or having any of the features discussed herein and achievable through the inventive hydrophilisation method.

Kit Containing a Microfabricated Device

A fourth aspect is a kit containing
(a) a microfabricated device comprising a liquid transportation system in which there are at least one chamber and/or at least one channel the walls of which comprises a synthetic polymer (plastics), and
(b) a fluorescent substance to be detected in the device, The kit is characterized in that the synthetic polymer material has a fluorescence that is non-significant in the same sense as discussed previously in this specification. The surfaces in the channels and chambers of the microfabricated device may wholly or partly be hydrophilised, for instance by gas plasma treatment, preferably according to the method described herein. With respect to the chemical composition of the plastics of the walls (surfaces) and its physical parameters, the same material with the same preferences as given above may be used.

Alternative hydrophilisation protocols are treatment with oxidating acids and with UV-oxidations, corona treatment, grafting and conventional coating with a polymer providing an increased number of polar groups, etc on the liquid contact surface of the material. The polar groups referred to are for instance hydroxy, amino, carboxy, amido, polethylene oxide etc.

Illustrative examples of fluorescent substances are fluorophores of organic or inorganic origin. In the former case they often have a low molecular weight (typically <1 kD). Important fluorophors have distinct emission wavelengths with distinct maxima in the interval 400–750 nm, with preference for the interval 480–670 nm. Fluorescein, phycocyanines that may be native or chemically modified, rhodamine, Texas Red, fluorescent rare earth chelates (in particular europium and terbium), cadmium selenide nanoparticles etc are typical examples. When in use the fluorophores may be in conjugate form, i.e. covalently attached to a reagent used. In this form the fluorescent substance typically has a molecular weight >1 kD. The kit, in particular the chambers and the channels combined with the fluorescent substance, may be used for running chemical reactions, assays, separations, cell culturing and the like as described elsewhere in this specification.

A Microfabricated Device

A fifth inventive aspect is a microfabricated device as defined above, in which the liquid transportation system is formed in/on a polymer material (plastics) in which the plastics essentially consist of one or more polymers obtained by polymerising one or more aliphatic monomers of the kind defined above. In this aspect the device may have one or more of the features of the other inventive aspects described in this specification. The same uses apply.

Cell Culturing

A sixth inventive aspect is a method for culturing cells. The term culturing of cells as used herein includes monolayer culture, suspension culture etc, and excludes culturing of cell aggregates, tissues, biopsies etc. Cell culturing as contemplated herein encompasses inherent normal cell culturing practice, for instance (a) The number of cells should be at least duplicated or at least triplicated during the cultivation period.

(b) Cultivation of anchorage-dependent cells, which represent an inhomogeneous phenotypic population, should take place under a low selection pressure for cell adherence to the surfaces used. This implies that for anchorage dependent cells the cell surface should be selected so that at least 30% of the plated cells should adhere to the substrate surface. More preferably, this adherence percentage should be above 50% or higher, such as at least 90%.

(c) In order to promote interaction between cells and substrate surfaces, cell adhesions factors are typically present in the culture medium. For mammalian adherent cells the culture medium typically contain up to 15% (w/w) serum according to well-established practice.

Culturing of cells, in particular anchorage-dependent cells, have previously been carried out in the presence of substrate surfaces made of plastics. The immediate water-contact angle has been 40°–60°. For cell culturing in microfabricated devices, there will be problems with liquid fluidics with this relatively low hydrophilicity.

It has now been found that culturing of various kinds of cells can be carried out in contact with superhydrophilic substrate surfaces made of plastics having an immediate water-contact angle that is significantly lower than 40°–60°. When applied to microfabricated devices this discovery will improve the situation with respect to liquid fluidics. The sixth aspect thus is characterized in that the cell culturing takes places in the presence of a surface made of plastics providing an immediate water-contact angle $\leq 30°$, such as $\leq 20°$. The surfaces are primarily provided on the inner walls of the culture vessel, but may also be provided by e.g. particles suspended in the vessel.

The immediate water-contact angle refers to hydrophilicities that preferably are stable against repeated washing as described above.

Surfaces that have been hydrophilised by gas plasma treatment as described in this specification are preferred. The preferred plasmas contain one or more gases that solely or in combination can introduce the mix of charged/polar groups discussed below. Among the gases tested, mixtures of oxygen and nitrogen are most preferred, with the individual gases being less preferred and with argon being least preferred. One can envisage that gases, such as sulphur dioxide and diphosphorous pentoxide, might be beneficial to use together with oxygen and/or nitrogen, if disregarding the handling problems they might give.

The most important factor for successful culture and behaviour of anchorage-dependent cells is the surface on which the cells grow. If this type of cells are plated onto a surface to which they cannot adhere or adhere poorly they will not grow. Cell function requires dynamic interactions between the cell and its substratum. These interactions occur at specialised contact sites where transmembrane proteins (integrins; Hynes R O, Integrins: versatility, modulation and signalling in cell adhesion. Cell 69: 11–25, 1992) link the interior of the cell with the external substratum. Surface functional groups and their charge character as well as hydrophilicity/hydrophobicity and surface free energy are important factors for cell behaviour (Lee J H et al., Biomaterials 18:351–358. 1997). Amine (ammonium), amide, hydroxyl, carboxyl (carboxylate) and sulphonyl (sulphonate) and sulphate groups at a suitable density are considered as sites for electrostatic interaction with the cell surface or attachment proteins and as mimicking adhesive contacts on extracellular matrix components (Maroudas, J. Theor. Biol. 49 (1975) 417–442; Lee et al., Biomaterials 15 (1994) 704–711; and Lee et al., Biomaterials 18 (1997) 351–358).

Non-anchorage dependent cells often require substrate surfaces during a certain part of their life cycle.

Typically the density of charged groups should be above 1–2 group per $Å^2$. As a thumb of rule smaller cells, such as HeLa cells (10–20 $\mu$m), require higher densities than larger cells, such as fibroblasts (about 30×100 $\mu$m), lower densities. The optimal values vary among cell types and may be determined as known in the art.

Cell culturing according to this aspect of the invention applies to a wide variety of cells. The cells may be anchorage- or non-anchorage-dependent. They may be of normal or tumour origin and they may be genetically manipulated in culture. They may be derived from mammals, bacteria, fungi (yeast), plants, fish, birds, amphibians, reptiles, etc. With respect to mammalian cells they may derive from any tissue, e.g. epithelial, endothelial, fibroblast, muscle, nerve, pigment, hematopoetic and germ cells.

For each respective kind of cell, the rules for selecting conditions and protocols are in principle the same as for culturing in other vessels and on particles.

The polymer surface material should not be toxic to the cells to be cultured. We have, for instance recognized, that gas plasma treated polymers built up of acrylo nitrile monomer or acrylate monomer may be toxic, probably due to degradation of the polymer. This may be circumvented by avoiding these kinds of material or by a proper post treatment of the material before it is used.

The invention will now be illustrated by non-limiting experiments. The invention is further defined in the appended claims that are part of the application text.

EXPERIMENTAL PART

Materials

Surfaces (discs): Polycarbonate of bisphenol A and polymethylmethacrylate CD blanks, injection molded at Toolex Alpha AB, Sundbyberg, Sweden. Non-patterned CD blanks, injection molded from Zeonex (a cycloolefin copolymer from Nippon Zeon, Japan) or Luran KR2536 (a styrene-acrylonitrile copolymer (SAN) from BASF, Germany) at Amic AB, Uppsala, Sweden). The planar (non-patterned) side of the discs were used in all experiments.

Gases: Oxygen, Argon and synthetic air were from 1 Air Liquide, France.

Plasma reactor: Plasma Science, PS0500 (BOC Coating Technology) main adjustable parameters: Radiofrequency (RF) power 0–500 W and gas flow 0–100 or 0–1000 sccm (standard $cm^3$/min).

Normally the reactor PS0500 is equipped with three electrode plates but after a rebuilding only one plate remained.

Methods

Washing: Before plasma treatment all discs were immersed in pro analysi isopropanol for 2 min, briefly flushed with 99% ethanol and blown dry with house nitrogen. This was done to remove any release agents, antistatic agents etc which might interfere with the plasma treatments.

Plasma treatments: The discs were placed in the plasma reactor in one of two positions; either on a plastic support 20.5 cm from the chamber floor or on glass supports placed on the electrode plate (45 cm from the chamber floor). After evacuation to a base pressure of 60 mTorr, the gas was let in and the gas flow adjusted to the desired level. The RF power was then switched on for the intended time and the reactor chamber was finally vented with ambient air.

Contact angle measurements: Directly after treatment, the equilibrium water-contact angle was measured with the sessile drop method on a Ramé-Hart goniometer bench. For each sample six measurements were made (two sides on each of three droplets). Contact angle measurements were also made after the pieces had been immersed for 2 min in 70% ethanol/water and blown dry with house nitrogen. The measurement was made within 20 s after the liquid had been applied in order to avoid changes in contact angle e.g. due to evaporation of the droplets.

Check for introduction of cross-links: The polymer material was dissolved in a suitable solvent for original polymer but not for polymer chains cross-linked during the plasma treatment before and after gas plasma treatments. The presence of any insoluble material after treatment was taken as an indication of introduction of cross-links.

Check for introduction of polar oxygen containing groups: Preliminary studies by ESCA showed that the pattern of these groups in the surface changed upon gas plasma treatment in a way suggesting an increase in surface bound oxygen. ESCA can be used to determine the various polar/charged groups that may be of importance for cell culturing.

Storage study: The plasma treated discs were placed in polystyrene Petri dishes and stored under ambient lab conditions. With regular intervals small pieces were cut off and the immediate water-contact angle measured both directly and after immersion in 70% ethanol/water. The cut-off samples were discarded after measurement.

Criteria for acceptance: From the hydrophilicity point of view the preliminary acceptance criterion was that the water-contact angle should be 20° or lower after washing in 70% ethanol.

Cell Culture:

Methods for Evaluating Surfaces:

Cell culture was used as a method for evaluation of the plasma-treated surfaces, since cells pose extremely high demands on their substratum.

Pieces of plasma-treated material were placed in multi-well plates, a suspension of cells in culture medium was added to each well and the plates were incubated in a cell culture atmosphere for various times. Cell adhesion, morphology and proliferation were evaluated microscopically and occasionally by the use of immunocytochemistry against cell proliferation markers and adhesive contacts. Preliminary results have revealed that the plasma-treated surfaces can be used for cell culture and that the cells exhibit necessary characteristics for optimal behaviour. Such characteristics include adhesion of nearly all of the plated cells in a evenly pattern, proper cell spreading on the material surface, signs of normal cell motility and cell division. Pathological signs including vacoles, excessive amounts of lysosomal granulae, blebbing or membrane destruction were insignificant. The cell lines tested so far include MRC5 (normal lung fibroblasts), HeLa (cervix carcinoma cells of epithelial-like origin), Chang (hepatoma, liver cells). The cells have been selected so that they will cover a wide range of demands on the surfaces. Non-anchorage dependent cells put very small demands on the surfaces as such. An example of such cells (Raji lymphoma), have been successfully cultured in the presence of the plasma-treated surfaces.

Our results suggest efficient cell culturing properties for our inventive plasma-hydrophilised surfaces. Efficient cell adhesion and growth could be accomplished for fibroblast-like cells on surfaces having water contact angels in the interval 10–40' and for epithelial like cells in the interval 5–40°.

Results

Planar CD Discs Plasma-Treated

Plasma Science PS0500 reactor with one electrode plate
Samples placed on a polypropylene support 20 cm from the reactor chamber floor in the center of the chamber

| Disc material | Gas | Gas flow set value sccm | RF power W | Power/flow W/sccm | Plasma time Min | Contact angle direct | Contact angle washed in 70% EtOH |
|---|---|---|---|---|---|---|---|
| polycarbonate | Oxygen | 15 | 500. | 33.33333 | 5 | 3 | 25 |
| polycarbonate | Oxygen | 15 | 300 | 20 | 5 | 3 | 38 |
| polycarbonate | Oxygen | 10 | 500 | 50 | 5 | 3 | 11 |

-continued

| Disc material | Gas | Gas flow set value sccm | RF power W | Power/flow W/sccm | Plasma time Min | Contact angle direct | Contact angle washed in 70% EtOH |
|---|---|---|---|---|---|---|---|
| polycarbonate | Oxygen | 10 | 300 | 30 | 5 | 4 | 31 |
| polycarbonate | Oxygen | 5 | 500 | 100 | 5 | 3 | 5 |
| polycarbonate | Oxygen | 5 | 300 | 60 | 5 | 4 | 16 |
| polycarbonate | Air (synth) | 25 | 500 | 20 | 5 | 4 | 17 |
| polycarbonate | Air (synth) | 25 | 300 | 12 | 5 | 10 | 33 |
| polycarbonate | Air (synth) | 5 | 500 | 100 | 5 | 3 | 2 |
| polycarbonate | Air (synth) | 5 | 300 | 60 | 5 | 4 | 13 |
| Polycarbonate | Argon | 100 | 500 | 5 | 5 | 25 | 48 |
| Polycarbonate | Argon | 100 | 300 | 3 | 5 | 27 | 56 |
| Polycarbonate | Argon | 25 | 500 | 20 | 5 | 4 | 18 |
| Polycarbonate | Argon | 25 | 300 | 12 | 5 | 9 | 39 |
| Polycarbonate | Argon | 5 | 500 | 100 | 5 | 4 | 3 |
| Polycarbonate | Argon | 5 | 300 | 60 | 5 | 4 | 9 |
| Zeonex | Oxygen | 100 | 500 | 5 | 5 | 20 | 29 |
| Zeonex | Oxygen | 100 | 300 | 3 | 5 | 17 | 34 |
| Zeonex | Oxygen | 50 | 500 | 10 | 5 | 10 | 5 |
| Zeonex | Oxygen | 50 | 300 | 6 | 5 | 15 | 28 |
| Zeonex | Oxygen | 25 | 500 | 20 | 5 | 7 | 4 |
| Zeonex | Oxygen | 25 | 300 | 12 | 5 | 11 | 10 |
| Zeonex | Oxygen | 5 | 500 | 100 | 5 | 4 | 2 |
| Zeonex | Oxygen | 5 | 300 | 60 | 5 | 4 | 4 |
| Zeonex | Air (synth) | 100 | 500 | 5 | 5 | 16 | 29 |
| Zeonex | Air (synth) | 100 | 300 | 3 | 5 | 16 | 36 |
| Zeonex | Air (synth) | 50 | 500 | 10 | 5 | 9 | 6 |
| Zeonex | Air (synth) | 50 | 300 | 6 | 5 | 15 | 26 |
| Zeonex | Air (synth) | 25 | 500 | 20 | 5 | 5 | 4 |
| Zeonex | Air (synth) | 25 | 300 | 12 | 5 | 9 | 6 |
| Zeonex | Air (synth) | 5 | 500 | 100 | 5 | 8 | 4 |
| Zeonex | Air (synth) | 5 | 300 | 60 | 5 | 5 | 4 |
| SAN | Oxygen | 100 | 500 | 5 | 5 | 8 | 27 |
| SAN | Oxygen | 100 | 300 | 3 | 5 | 11 | 23 |
| SAN | Oxygen | 50 | 500 | 10 | 5 | 8 | 7 |
| SAN | Oxygen | 50 | 300 | 6 | 5 | 9 | 22 |
| SAN | Oxygen | 25 | 500 | 20 | 5 | 5 | 7 |
| SAN | Oxygen | 25 | 300 | 12 | 5 | 7 | 14 |
| SAN | Oxygen | 5 | 500 | 100 | 5 | 4 | 2 |
| SAN | Oxygen | 5 | 300 | 60 | 5 | 5 | 3 |
| SAN | Air (synth) | 100 | 500 | 5 | 5 | 8 | 27 |
| SAN | Air (synth) | 100 | 300 | 3 | 5 | 8 | 26 |
| SAN | Air (synth) | 50 | 500 | 10 | 5 | 7 | 8 |
| SAN | Air (synth) | 50 | 300 | 6 | 5 | 8 | 26 |
| SAN | Air (synth) | 25 | 500 | 20 | 5 | 4 | 5 |
| SAN | Air (synth) | 25 | 300 | 12 | 5 | 6 | 12 |
| SAN | Air (synth) | 5 | 500 | 100 | 5 | 5 | 4 |
| SAN | Air (synth) | 5 | 300 | 60 | 5 | 4 | 4 |
| PMMA | Air (synth) | 50 | 500 | 10 | 5 | 20 | 40 |
| PMMA | Air (synth) | 50 | 300 | 6 | 5 | 39 | 53 |
| PMMA | Air (synth) | 25 | 500 | 20 | 5 | 8 | 21 |
| PMMA | Air (synth) | 25 | 300 | 12 | 5 | 26 | 44 |
| PMMA | Air (synth) | 10 | 500 | 50 | 5 | 4 | 4 |
| PMMA | Air (synth) | 10 | 300 | 30 | 5 | 6 | 14 |
| PMMA | Air (synth) | 5 | 500 | 100 | 5 | 8 | 4 |
| PMMA | Air (synth) | 5 | 300 | 60 | 5 | 5 | 3 |
| PMMA | Oxygen | 50 | 500 | 10 | 5 | 29 | 54 |
| PMMA | Oxygen | 50 | 300 | 6 | 5 | 39 | 52 |
| PMMA | Oxygen | 25 | 500 | 20 | 5 | 11 | 40 |
| PMMA | Oxygen | 25 | 300 | 12 | 5 | 31 | 53 |
| PMMA | Oxygen | 10 | 500 | 50 | 5 | 5 | 10 |
| PMMA | Oxygen | 10 | 300 | 30 | 5 | 7 | 45 |
| PMMA | Oxygen | 5 | 500 | 100 | 5 | 4 | 4 |
| PMMA | Oxygen | 5 | 300 | 60 | 5 | 4 | 7 |

What is claimed is:

1. A method for decreasing the immediate water-contact angle of a substrate surface, such that said decreased angle remains for at least one month, wherein said substrate surface is made of plastic and comprises a channel, having a depth of $\leq 1000$ μm, to serve as a liquid transportation system, said method comprises treating the substrate surface with a gas plasma of a non-polymerizable gas under conditions, wherein the intensity of the plasma is >5 W/cm$^3$/min, the power is $\geq 250$ W and the gas flow is $\leq 50$ cm$^3$/min to produce a treated material having an immediate water-contact angle of <30° after washing said treated substrate with a mixture of pure water and ethanol, wherein said contact angle remains for at least one month.

2. The method of claim 1, wherein the plastic material comprises a polymer comprising an unsaturated monomer and/or a condensation polymer.

3. The method of claim 1, wherein the plasma is induced by radiowaves, microwaves, or a combination thereof.

4. The method of claim 1, wherein the plasma gas is selected from the group consisting of oxygen, nitrogen, noble gas, or a mixture thereof.

5. The method of claim 1, wherein subsequent to the treating step, the surface of the substrate is derivatized to exhibit anion exchanging groups, cation exchanging groups, amphoteric groups, hydroxy groups, bioaffinity groups, or chelating groups.

6. A substrate surface, which is made of a plastic material and comprises a channel having a depth of $\leq 1000$ μm to serve as a liquid transportation system, said substrate surface has been plasma treated with a gas plasma of a non-polymerizable gas under conditions wherein the intensity of the plasma is >5 W/cm$^3$/min, the power is $\geq 250$ W and the gas flow is $\leq 50$ cm$^3$/min to produce a treated material having an immediate water-contact angle of <30°, wherein said water-contact angle is changed less than 20% and/or less than 5° upon washing with a 70% w/w ethanol/water mixture and said water-contact angle remains for at least one month.

7. The substrate surface of claim 6, wherein the plastic material is a polymer comprising an unsaturated monomer and/or a condensation polymer.

8. The substrate surface of claim 6, wherein the surface before having been gas plasma treated exhibits an immediate water-contact angle >30°.

9. A method for culturing anchorage-dependent cells and non-anchorage dependent cells that in a part of their life cycle require attachment to a substrate surface comprising performing the culturing of the cells in contact with a substrate surface which is made of a plastic material, said substrate surface has been plasma treated with a gas plasma of a non-polymerizable gas under conditions wherein the intensity of the plasma is >5 W/cm$^3$/min, the power is $\geq 250$ W and the gas flow is $\leq 50$ cm$^3$/min to produce a treated material having an immediate water-contact angle of <30° that is changed less than 20% and/or less than 5° upon washing with a 70% w/w ethanol/water mixture and said water-contact angle remains for at least one month, said culturing is preformed in a chamber providing said substrate surface which is present in a liquid transportation system of a microfabricated device comprising a channel having a depth of $\leq 1000$ μm in said chamber.

10. The method of 9, wherein the cells are anchorage dependent and the substrate surface enables at least 30% of the plated cells to adhere to the substrate surface.

11. The method of claim 9, wherein at most 15% of the culture medium is serum.

12. The method of claim 9, wherein culturing is taking place during a time period permitting the number of cells to be at least duplicated.

13. The method according to claim 2, wherein said polymer is a copolymer.

14. The method according to claim 2, wherein said unsaturated monomer is an alkene, alkadiene or a vinyl aryl compound.

15. The method according to claim 14, wherein said alkene/alkadiene is selected from the group consisting of acids, esters, amides, and nitrites containing one or more alkene groups.

16. The substrate surface of claim 6, wherein said polymer is a copolymer.

17. The substrate surface of claim 7, wherein said unsaturated monomer is an alkene, alkadiene or a vinyl aryl compound.

18. The substrate surface of claim 17, wherein said alkene/alkadiene is selected from the group consisting of acids, esters, amides, and nitrites containing one or more alkene groups.

19. The substrate surface of claim 7, wherein said polymer material is cross-linked.

20. The substrate surface of claim 7, wherein said polymer material is a mixture of two or more polymers or copolymers.

21. The method of claim 2, wherein said condensation polymer comprises a monomer having two or more groups selected from the group consisting of an amino group, a hydroxy group and a carboxy group.

22. The substrate surface of claim 7, wherein said condensation polymer comprises a monomer having two or more groups selected from the group consisting of an amino group, a hydroxy group and a carboxy group.

* * * * *